US008380266B2

(12) United States Patent
Vaughan et al.

(10) Patent No.: US 8,380,266 B2
(45) Date of Patent: Feb. 19, 2013

(54) COIL ELEMENT DECOUPLING FOR MRI

(75) Inventors: J. Thomas Vaughan, Minneapolis, MN (US); Jinfeng Tian, Falcon Heights, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 13/124,206

(22) PCT Filed: Oct. 15, 2009

(86) PCT No.: PCT/US2009/060841
§ 371 (c)(1),
(2), (4) Date: Apr. 14, 2011

(87) PCT Pub. No.: WO2010/045457
PCT Pub. Date: Apr. 22, 2010

(65) Prior Publication Data
US 2011/0312499 A1      Dec. 22, 2011

Related U.S. Application Data

(60) Provisional application No. 61/105,678, filed on Oct. 15, 2008.

(51) Int. Cl.
*H01B 12/00* (2006.01)
*H01F 6/00* (2006.01)

(52) U.S. Cl. ...................................................... 505/211
(58) Field of Classification Search ................. 505/211, 505/213; 324/318
See application file for complete search history.

(56) References Cited

U.S. PATENT DOCUMENTS

| 6,633,161 B1 * | 10/2003 | Vaughan, Jr. ............... 324/318 |
| 7,015,696 B2 * | 3/2006 | Kabasawa ..................... 324/318 |
| 7,109,713 B2 * | 9/2006 | Okamoto et al. ............ 324/318 |
| 7,205,765 B2 * | 4/2007 | Machida et al. ............. 324/318 |
| 2004/0155656 A1 | 8/2004 | Leussler |
| 2008/0129294 A1 | 6/2008 | Leussler |

FOREIGN PATENT DOCUMENTS
WO    WO 2006/090293 A2 *    8/2006

* cited by examiner

*Primary Examiner* — Colleen Dunn
(74) *Attorney, Agent, or Firm* — Seager, Tufte & Wickhem LLC

(57) ABSTRACT

An RF coil adjacent an imaging region includes a plurality of conducting coil elements, with each conducting coil element including a proximal portion and a distal portion. The RF coil also includes a capacitance between the distal portions of the at least two conducting coil elements. A mutual coupling inductance between at least two conducting coil elements of the plurality of conducting coil elements is substantially cancelled by the capacitance between the distal portions of the at least two conducting coil elements.

20 Claims, 13 Drawing Sheets

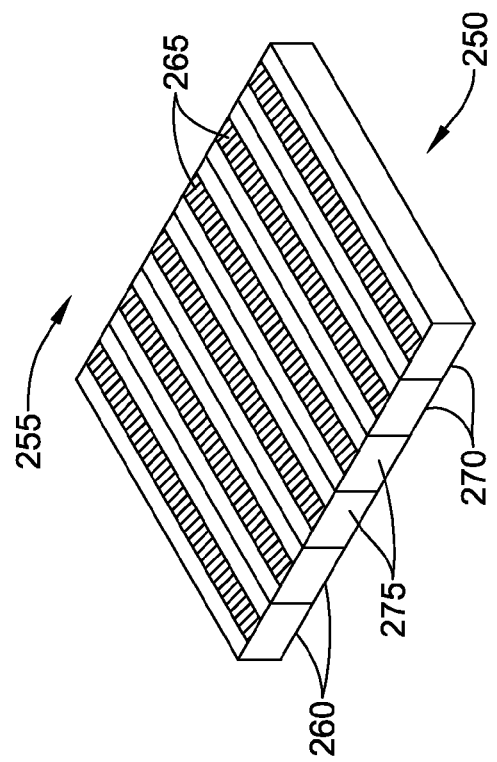
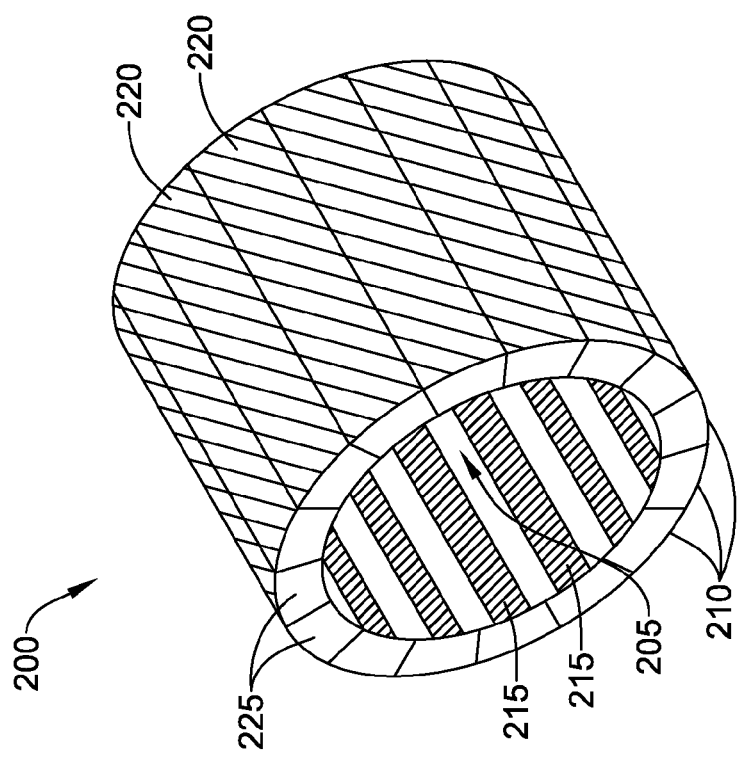
Figure 2B
Figure 2A

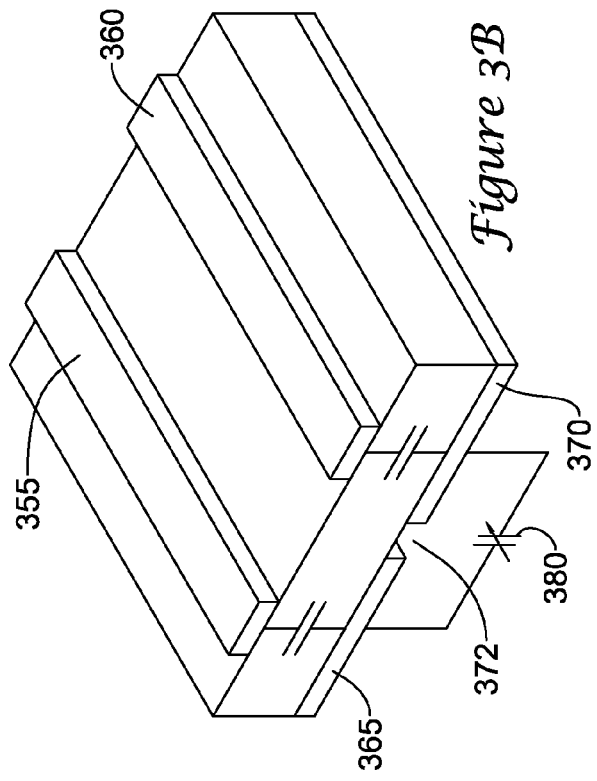
Figure 3B
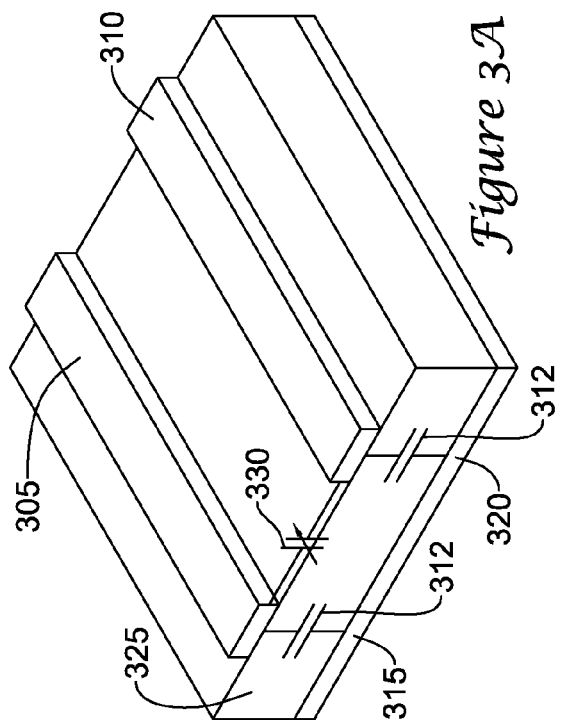
Figure 3A
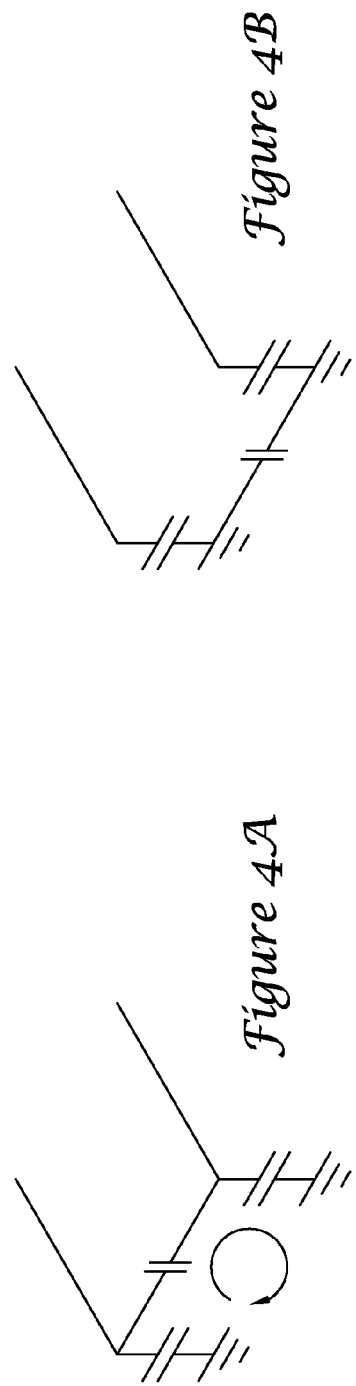
Figure 4B
Figure 4A

COIL ELEMENT DECOUPLING FOR MRI

RELATED APPLICATION

This application claims priority to U.S. Provisional Patent Application Ser. No. 61/105,678, filed Oct. 15, 2008, and entitled "COIL ELEMENT DECOUPLING FOR MRI," J. Thomas Vaughan et al., which is hereby incorporated by reference.

GOVERNMENT RIGHTS

The present subject matter was partially supported under NIH contract numbers EB000895-04 and EB006835. The United States government may have has certain rights in the invention.

TECHNICAL FIELD

The present disclosure relates generally to radio frequency (RF) coils for RF field generation and detection, and more particularly, to RF coils used for magnetic resonance imaging.

BACKGROUND

Nuclear magnetic resonance (NMR) or magnetic resonance imaging (MM), functional MRI (fMRI), electron spin resonance (ESR) or electron paramagnetic resonance (EPR) and other imaging techniques using RF field generating coils are finding increasing utility in applications involving imaging of various parts of the human body, of other organisms, whether living or dead, and of other materials or objects requiring imaging or spectroscopy.

Magnetic Resonance Imaging (MRI) generally utilizes hydrogen nuclear spins of the water molecules in the subject (which may be a human body, other organism, or non-organism), although other nuclear spins have been used as well. The spins are polarized by a strong, uniform, static magnetic field (conventionally denoted as $B_0$) typically generated by a superconducting magnet. The magnetically polarized nuclear spins generate magnetic moments in the subject. The magnetic moments point or are aligned parallel to the direction of the main magnetic field $B_0$ in a steady state and generally do not produce useful information if they are not disturbed by any excitation.

The generation of nuclear magnetic resonance (NMR) signals for MRI data acquisition may be accomplished by exciting the magnetic moments with a uniform radio-frequency (RF) magnetic field (typically referred to as the $B_1$ field or the excitation field), for example, by applying a uniform RF magnetic field orthogonal to $B_0$. This RF field typically is centered on the Larmor frequency of protons in the $B_0$ field and causes the magnetic moments to mutate their alignment away from $B_0$. The $B_1$ field typically is produced in the imaging region of interest by an RF transmit or drive coil that is driven by a computer-controlled RF transmitter with a RF power amplifier. During excitation, the nuclear spin system absorbs magnetic energy, and the magnetic moments process around the direction of the main magnetic field. After excitation, the processing magnetic moments go through a decay process, release their absorbed energy, and return to a steady state. During the decay process, NMR signals may be detected by the use of a receive RF coil that is placed in the vicinity of the excited volume of a subject. The NMR signal is an electrical voltage or current in the receive RF coil that has been induced by the flux change over a period of time due to the relaxation of processing magnetic moments. In a conventional MRI system, imaging may be assisted by the use of additional pulsed magnetic gradient fields to result in selective excitation of specific volumes of the subject, thus spatially encoding the NMR signal to correspond to those specific volumes. These gradient field may be generated by gradient coils integrated inside the main magnet system.

A recent trend in MRI technology has been the development of sophisticated multi-element phased array coils that are capable of acquiring multiple channels of data in parallel. Such "parallel imaging" techniques may have a number of advantages, such as accelerated imaging, in some cases by replacing some of the spatial coding originating from the magnetic gradients with the spatial sensitivity of the different coil elements.

There is an ongoing need for new and improved RF coils, including coils used for parallel imaging.

SUMMARY

The present disclosure relates generally to radio frequency (RF) coils for RF field generation and detection, and more particularly, to decoupling current elements of RF coils used for magnetic resonance imaging.

In one aspect, the present disclosure provides a radio frequency (RF) coil adjacent an imaging region. The RF coil includes a plurality of conducting coil elements, with each conducting coil element including a proximal portion and a distal portion. "Proximal" and "distal" are considered relative to the imaging region. The RF coil also includes a capacitance between the distal portions of the at least two conducting coil elements. A mutual coupling inductance between at least two conducting coil elements of the plurality of conducting coil elements is substantially cancelled by the capacitance between the distal portions of the at least two conducting coil elements.

In another aspect, the present disclosure provides a magnetic resonance imaging system. The magnetic resonance imaging system includes a superconducting magnet, a gradient coil system, and an RF coil adjacent an imaging region. The RF coil includes a plurality of conducting coil elements, with each conducting coil element including a proximal portion and a distal portion. "Proximal" and "distal" are considered relative to the imaging region. The RF coil also includes a capacitance between the distal portions of the at least two conducting coil elements. A mutual coupling inductance between at least two conducting coil elements of the plurality of conducting coil elements is substantially cancelled by the capacitance between the distal portions of the at least two conducting coil elements.

In yet another aspect, the present disclosure provides a method for balancing an RF imaging coil having a plurality of independent current elements. The method includes the steps of selecting an RF imaging coil design to achieve specified imaging objectives, identifying a pair of current elements of the plurality of independent current elements, and modifying distal portions of the pair of current elements to result in a reduced mutual coupling inductance between the pair of current elements below an acceptable threshold inductance value.

The above summary is not intended to describe each and every disclosed embodiment or every implementation of the disclosure. The Description that follows more particularly exemplifies the various illustrative embodiments.

BRIEF DESCRIPTION OF THE FIGURES

The following description should be read with reference to the drawings. The drawings, which are not necessarily to scale, depict selected embodiments and are not intended to limit the scope of the disclosure. The disclosure may be more completely understood in consideration of the following detailed description of various embodiments in connection with the accompanying drawings, in which:

FIG. 2A is a schematic diagram of an illustrative multi-channel RF coil in a generally cylindrical configuration;

FIG. 2B is a schematic diagram of an illustrative multi-channel RF coil in a generally planar or flat configuration;

FIG. 3A is a schematic diagram of two illustrative coil elements of a multichannel RF coil showing coil decoupling at the proximal portions of the coil elements;

FIG. 3B is a schematic diagram of two illustrative coil elements of a multichannel RF coil showing coil decoupling at the distal portions of the coil elements;

FIG. 4A is a schematic circuit diagram corresponding to the RF coil configuration of FIG. 3A;

FIG. 4B is a schematic circuit diagram corresponding to the RF coil configuration of FIG. 3B;

DESCRIPTION

The following description should be read with reference to the drawings. The drawings, which are not necessarily to scale, depict selected embodiments and are not intended to limit the scope of the invention. Although examples of construction, dimensions, and materials are illustrated for the various elements, those skilled in the art will recognize that many of the examples provided have suitable alternatives that may be utilized.

Figure 1:
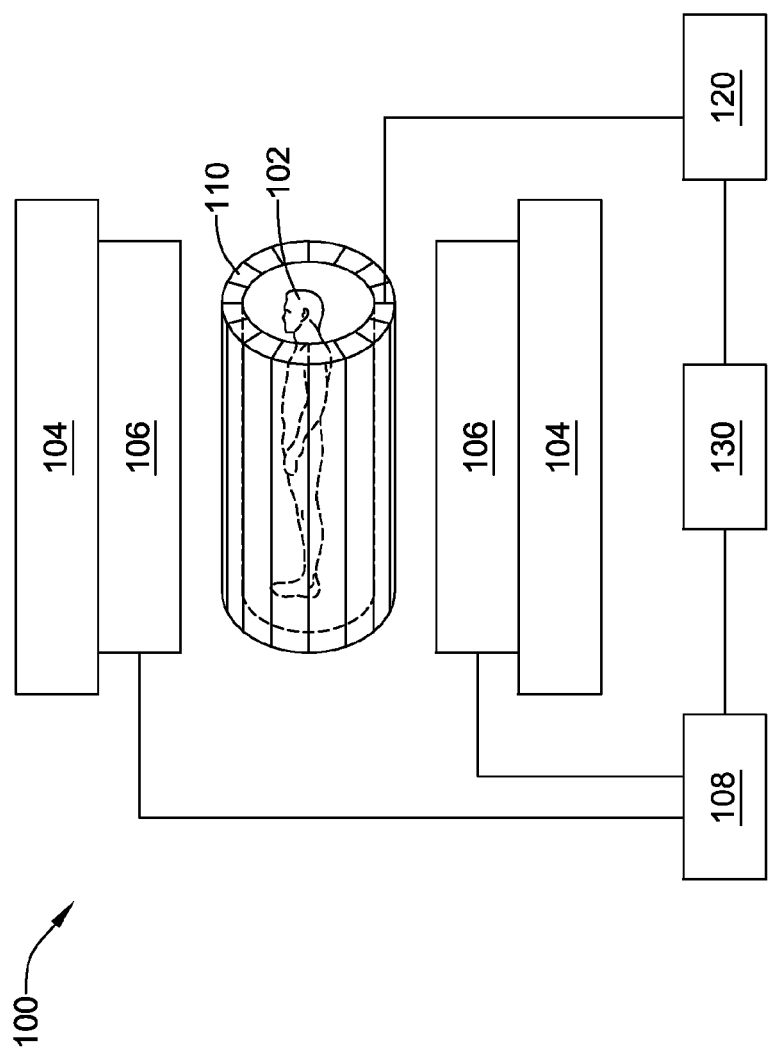
FIG. 1 is a schematic diagram of an illustrative magnetic resonance imaging system.

FIG. 1 is a schematic diagram of an illustrative magnetic resonance imaging system 100 in accordance with the present disclosure. MRI system 100 may be used to image a subject or patient 102. MRI system 100 includes a superconducting magnet 104 and gradient coils 106 that are coupled to gradient coil control components 108. The system 100 also includes an RF coil system that includes a multi-channel RF coil 110 connected to a multi-channel RF transceiver 120. RF coil 110 is schematically illustrated as a whole-body coil, but this is not necessary; the coil may be considerably smaller and may be used in conjunction of imaging of smaller body parts or other object of interest. Gradient control components 108 and multi-channel RF transceiver 120 are connected to MRI system controller 130. MRI system 100 may include any other suitable components, such as additional RF coils, other devices for imaging or positioning, other monitoring or therapeutic instruments, and so on.

RF coil 110 may be an RF coil as described in U.S. Pat. No. 6,633,161 ("RF COIL FOR IMAGING SYSTEM," Vaughan) or U.S. Pat. No. 5,557,247 ("RADIO FREQUENCY VOLUME COILS FOR IMAGING AND SPECTROSCOPY," Vaughan), both of which are hereby incorporated by reference, or it may be any other suitable RF coil. Suitable coils include, but are not limited to, coils having multi-channel arrays, including TEM coils including one or more independent transmission line elements, stripline arrays, microstrip arrays, transmission line arrays, and the like. In some cases, the coils may have independent phase and magnitude control. RF coil 110 may be a volume coil, generally defined as a coil with a plurality of current elements (coil elements) surrounding a volume containing an NMR active sample, or a surface coil, generally defined as a coil with one or more elements adjacent to an NMR active sample. RF coil 110 may be a coil structured appropriately for imaging of a particular external or internal anatomical region, such as the head, knee, elbow, breast, heart, etc., or it may be a body coil for imaging substantially an entire body or major subportion of a body. RF coil 110 may include one or more independent current elements, on which field generating currents may be controlled in magnitude, phase, frequency, space, and time. RF coil 110 may be used for MRI parallel imaging in any appropriate parallel imaging method, but RF coils of the present disclosure are not limited to use in parallel imaging.

An RF coil of the present disclosure may be a transmit coil, a receive coil, or both. A subset of coil elements of an RF coil may serve as transmitters, and another subset may serve as receivers. Such subsets may be exclusive in membership, they may intersect in membership, or they may include the same member coil elements. Some coil elements may serve as transmit coil elements during some temporal periods, and receive coil elements during other temporal periods. A coil may include multiple transmit subsets and/or multiple receive subsets. Different subsets may target different imaging volumes, and/or may target different magnetic moments. Membership of coil elements in subsets may vary dynamically depending on imaging goals and needs. In general, a coil may be configured arbitrarily and used such that any subset of coil elements may be employed at any given time for transmit or receive purposes, independent of the use of the coil elements of the subset at any other time during an imaging session.

RF coils systems as described herein may be useful for human head and body imaging at high magnetic field strengths, but are not necessarily limited to such high magnetic field strengths. RF coil systems of the present disclosure may be used in imaging systems employing magnetic field strengths of 1.5 T, 4 T, 4.1 T, 7 T, 8 T, 9.4 T, and any other suitable field strengths.

FIG. 2A is a schematic diagram of an illustrative multi-channel RF coil 200 in a generally cylindrical configuration, although any suitable coil geometry may be used. RF coil 200 may be used, for example, as RF coil 110 of FIG. 1, or in any other appropriate apparatus using an RF coil. RF coil 200 surrounds a volume, including an imaging region 205. RF coil 200 may be a transmit coil and/or a receive coil for interacting with the imaging region 205. RF Coil 200 includes a plurality of conductive coil elements 210. RF coil 200 may have 1, 2, 4, 8, 16, 32, 64, or any other suitable number of coil elements, which may also be referred to as channels. Each coil element 210 may have a proximal portion 215 and a distal portion 220, where proximal and distal describe the location of the portion relative to the imaging region 205. Proximal and distal portions 215, 220 of coil elements 210 may be capacitively coupled. In some coils, the distal portions 220 of the coil elements 210 may be formed together as a single conductor, or as multiple conductors numbering less than the number of coil elements. The proximal portions 220 may form a shield, ground shield, ground plane, sidewall, reflector, or the like. Dielectric material 225 may occupy space between the proximal and distal portions 215, 220 of the coil elements 210.

FIG. 2B is a schematic diagram of an illustrative multi-channel RF coil 250 in a generally planar or flat configuration, although any suitable coil geometry may be used. RF coil 250 may be used, for example, as RF coil 110 of FIG. 1, or in any other appropriate apparatus using an RF coil. RF coil 250 may share design similarities to RF coil 200 of FIG. 2a. RF coil 250 may be a transmit coil and/or a receive coil for interacting with an imaging region 255 adjacent coil 250. RF Coil 250 includes a plurality of conductive coil elements 260. RF coil 250 may have any suitable number of coil elements, which may also be referred to as channels. Each coil element 260 may have a proximal portion 265 and a distal portion 270, where proximal and distal describe the location of the portion relative to the imaging region 255. Proximal and distal portions 265, 270 of coil elements 260 may be capacitively coupled. In some coils, the distal portions 270 of the coil elements 260 may be formed together as a single conductor, or as multiple conductors numbering less than the number of coil elements. The proximal portions 270 may form a shield, ground shield, ground plane, sidewall, reflector, or the like. Dielectric material 275 may occupy space between the proximal and distal portions 265, 270 of the coil elements 260.

In many applications, coil elements of a multi-channel RF coil such as coils 110, 200, and 300, or any other appropriate coil are to act independently for transmit or receive functions. Multi-channel RF transceiver 120 may be configured to address coil elements individually, or collectively for sets, or for all channels in transmission (excitation) and/or reception modes. Multi-channel RF transceiver 120 may be a transceiver as described in U.S. Pat. No. 6,969,992 ("PARALLEL TRANSCEIVER FOR NUCLEAR MANGETIC RESONANCE SYSTEM," Vaughan et al.), which is hereby incorporated by reference, or it may be any other suitable RF transceiver.

While a multi-channel RF transceiver may be configured to address individual coil elements independently, the electrodynamic properties of an RF coil may result in interactions between coil elements, such as a changing current in one coil element inducing a current in another coil element. In some cases, such interactions may be desirably exploited, such as in a drive mode where one set of drive coil elements are directly driven by an RF transceiver, while another set of drive coil elements are inductively driven from the directly-driven set. In other cases, though, it may be desirable to decouple coil elements from each other such that currents in one coil element induce significantly reduced currents, or no currents, in other coil elements. The present disclosure provides structures and methods for decoupling coil elements in RF coils.

One method for decoupling coil elements of an RF coil is illustrated in FIG. 3A. FIG. 3A is a schematic diagram of two illustrative coil elements of a multichannel RF coil showing coil decoupling at the proximal portions of the coil elements. The two coil elements of FIG. 3A may be the only coil elements of the RF coil, or they may be two of a larger plurality of coil elements. The coil elements may be similar or like those of RF coils 110, 200, 300, or any other compatible RF coil. In FIG. 3A, a first proximal portion 305 of a first current element is disposed adjacent a second proximal portion 310 of a second current element. While the two current elements in FIG. 3A are illustrated as directly neighboring, without other current element in between, this is not necessary, and there may be other current elements disposed between the two (not shown). (Frequently, however, the strongest mutual inductances will exist between the closest neighboring current elements.) First and second proximal portions 305, 310 of the first and second coil elements may be capacitively coupled at both ends (only one end is seen in the figure, with coupling capacitors 312) to their respective first and second distal portions 315, 320, thus forming first and second coil element current loops. In FIG. 3A, the first and second distal portions 315 and 320 of the current elements are shown as a single piece, but this is not necessary; they may be separate portions, as in the configuration of FIG. 3B, where the distal portions are separated. The first and second distal portions 315, 320 may be considered to form a shield, ground shield, ground plane, etc. First and second proximal portions 305, 310 may be disposed generally parallel to each other. First and second distal portions 315 and 320 may be disposed generally parallel to their respective proximal portions. A continuous or discontinuous dielectric material 325 may be disposed between the proximal and distal portions of the current loops.

The geometry of the first and second coil element current loops may generally result in a mutual coupling inductance between the loops, such that a time-varying current in one may induce a current in the other. In the configuration of FIG. 3A, a bridge capacitor 330 coupling the first and second proximal portions 305, 310 may act to decouple this mutual coupling inductance. Bridge capacitor 330 is shown as a variable capacitor to suggest that its value may be tuned. For a given mutual coupling inductance (without the bridge capacitor 330), an appropriate value of capacitance may critically cancel the inductance to decouple the first and second coil elements.

While FIG. 3A and other figures of this disclosure depict structures and methods for decoupling pairs of coil elements, it should be understood that RF coils having greater numbers of coil elements may include multiple instances of the decoupling structures and methods disclosed herein, to achieve decoupling of multiple pairs of coil elements. In some embodiments, many, most, or all immediately neighboring pairs of coil elements of RF coils are decoupled with the teachings of this disclosure. In some embodiments, symmetry of the RF coils allow the same decoupling structures to be used in multiple locations to decouple multiple symmetric pairs of coil elements. The structures and methods of this disclosure may be replicated as appropriate to effect decoupling in any suitable RF coil configuration.

The introduction of bridge capacitor 330, while it may reduce or cancel mutual coupling inductance between coil elements, introduces one or more new current loops to the RF coil. One new current loop, for example, is defined by the path travelling across the bridge capacitor 330 from the first proximal portion 305 to the second proximal portion 310, down through a coupling capacitor 312 to the distal portions 320, 315, and back up through the other coupling capacitor 312. This loop is represented in the schematic circuit diagram of FIG. 4A, corresponding to the RF coil configuration of FIG. 3A. Such a new current loop formed by the introduction of bridge capacitor 330 may affect the RF coil in potentially undesirable ways. For example, it may lower the Q of resonant coil elements of the RF coil, thus lowering RF coil efficiency. It may create new circuit resonances of its own. Current flowing in the new current loop forms a magnetic dipole, adding a potentially unwanted magnetic field component in the imaging region of the RF coil that may significantly degrade field uniformity.

An improved arrangement for substantially cancelling mutual coupling inductances between coil elements of RF coils is shown in FIG. 3B. FIG. 3B is a schematic diagram of two illustrative coil elements of a multichannel RF coil showing coil decoupling at the distal portions of the coil elements. The RF coil configuration of FIG. 3B is similar many regards to that of FIG. 3A, but with some differences. In FIG. 3B, distal portions 365 and 370 are separated by a gap 372, which may be a narrow slit. (In general, the figures are not to scale, and in particular, the width of the gap/slit 372 In contrast to the configuration of FIG. 3A, in FIG. 3B the first and second coil element current loops may be decoupled by capacitance between the first and second distal portions 365, 370 of the first and second current elements, which may also be considered part of a shield, ground shield, sidewall, etc., of the RF coil. A capacitance in general exists between any two conductors, and hence, there is a capacitance between the distal portions 365, 370 without further added structure. However, an additional capacitance 380 is represented in FIG. 3B with a variable capacitor, to indicate that adding an appropriate value of capacitance may critically cancel the inductance to decouple the first and second coil elements. This decoupling of the first and second coil elements may be achieved without a bridge capacitor such as capacitor 330 of FIG. 3A coupling the first and second proximal portions 355, 360 of the coil elements of FIG. 3B.

As suggested by the schematic circuit diagram of FIG. 4B, corresponding to the RF coil configuration of FIG. 3B, the decoupling arrangement involving capacitive coupling of the distal portions 365, 370 of the coil elements does not result in the potentially deleterious new current loop(s) introduced by the introduction of the bridge capacitor 330 of FIG. 3A. Furthermore, decoupling current travelling through decoupling capacitance 380 is located farther from the imaging region, and fields created by the decoupling current are shielded at least in part by the proxial 355, 360 and distal 365, 370 portions of the coil elements.

The distal portions 365, 370 of the RF Coil of FIG. 3B may be modified in a number of ways to vary their capacitance to result in decoupling. These, or any other distal portions, may be coupled with one or more lumped (discrete) capacitors, or they may be capacitively coupled by distributed capacitance, as illustrated in further detail herein. Furthermore, combinations of distributed and discrete capacitance may be used; for example, distributed capacitance may provide the majority of capacitance between distal portions, with additional fine-tuning provided by discrete trimmer capacitors.

The amount of capacitance for decoupling coil elements may be selected by a variety of methods. The amount of decoupling capacitance may be chosen to result in reducing the mutual coupling inductance between coil elements to below an acceptable threshold inductance value. The amount of capacitance generally varies depending on the reactance of the coil elements in the absence of additional decoupling capacitance. This reactance may be empirically measured or calculated, and an appropriate capacitance selected. The capacitance may be empirically adjusted in a feedback process to arrive at a desired level of decoupling. Optimization algorithms may be used to adjust decoupling. Some of these methods may be practiced in situ, during an imaging session with a subject, the presence of which may affect reactance in the RF coil.

EXAMPLES

The decoupling methods of the following examples may be applied to RF coils 110, 200, 300, or any other suitable RF coils.

Two-Channel Coil Array with No Decoupling

Figure 5:
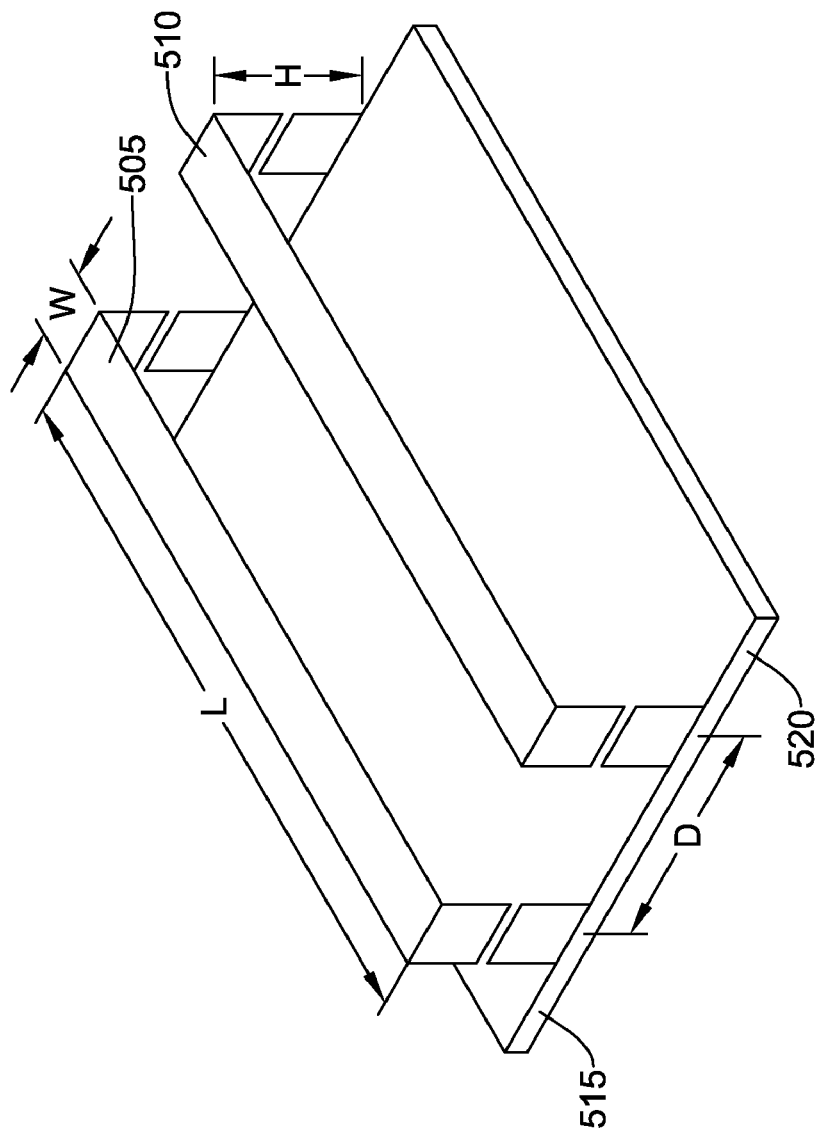
FIG. 5 is a schematic diagram of a computationally simulated RF coil arrangement having no decoupling.

The mutual coupling inductance of a two-channel (i.e., two coil element) RF coil is computationally simulated. FIG. 5 is a schematic diagram of the simulated coil arrangement. The RF coil includes first and second proximal portions 505, 510 capacitively coupled (represented by the gaps in the vertical sections) to distal portions 515, 520. In this model, the distal portions are a unitary piece. For clarity, dielectric material between the proximal and distal portions is not shown. The proximal portions have widths of W=10 mm and lengths of L=150 mm. The dielectric thickness is H=20 mm. The coil elements are spaced apart by D=50 mm.

In the simulation, one of the coil elements is driven over a range of RF frequencies and the resonant response of the coil is calculated. The coil element is coupled to the drive circuitry (not shown) at the near (left) side, as illustrated. The current in the driven coil and the induced current in the non-driven coil element is calculated. At the resonance peak (in the approximate vicinity of 300 MHz for all the calculated examples), the ratio of the induced current to the current in the driven coil element is denoted $I_2/I_1$. In this example, $I_2/I_1=47\%=-6.5$ dB. The induced current has a magnitude of 47% of the current in the driven coil, or a current 6.5 dB lower than the driven current.

Figure 6:
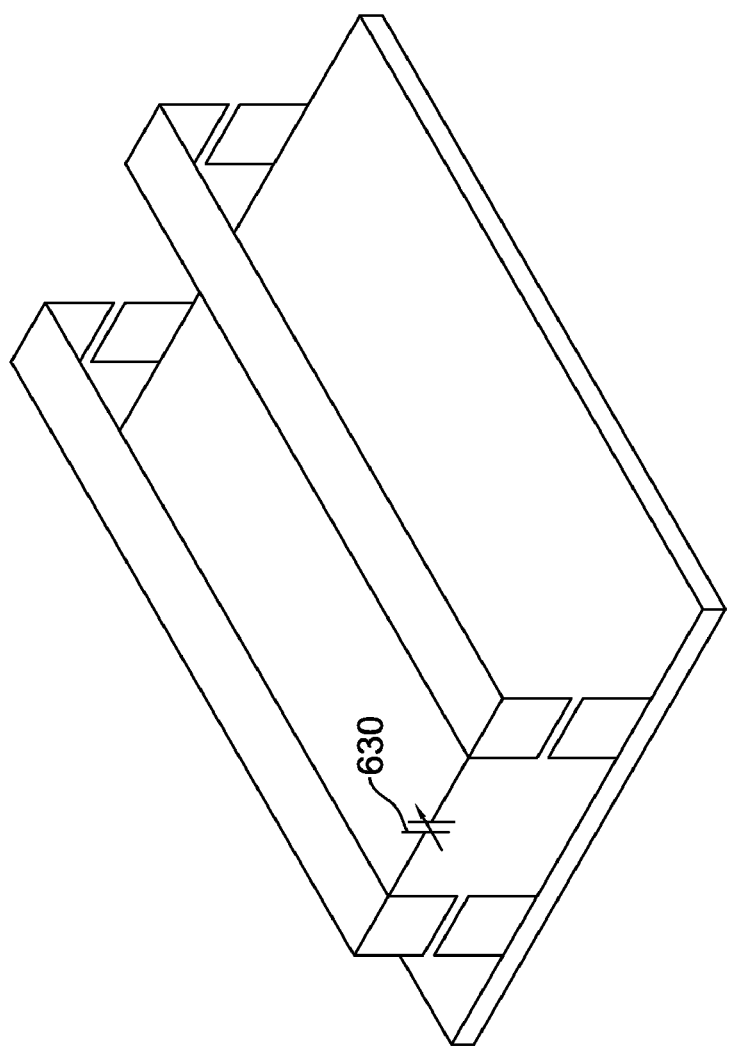
FIG. 6 is a schematic diagram of a computationally simulated RF coil arrangement having bridge capacitance decoupling between proximal portions.

Two-Channel Coil Array with Bridge Capacitance Decoupling Between Proximal Portions In this example, schematically illustrated in FIG. 6, the geometry is like that of the example of FIG. 5, with the addition of a discrete (lumped) decoupling bridge capacitance 630 having a value of 1.18 pF between the proximal portions. The value of the decoupling bridge capacitance 630 is selected to critically cancel the calculated mutual coupling inductance between the coil elements in the absence of a decoupling capacitance. The computed ratio of the induced current to the current in the driven coil element at resonance is $I_2/I_1=16.5\%=-15.7$ dB.

Figure 7:
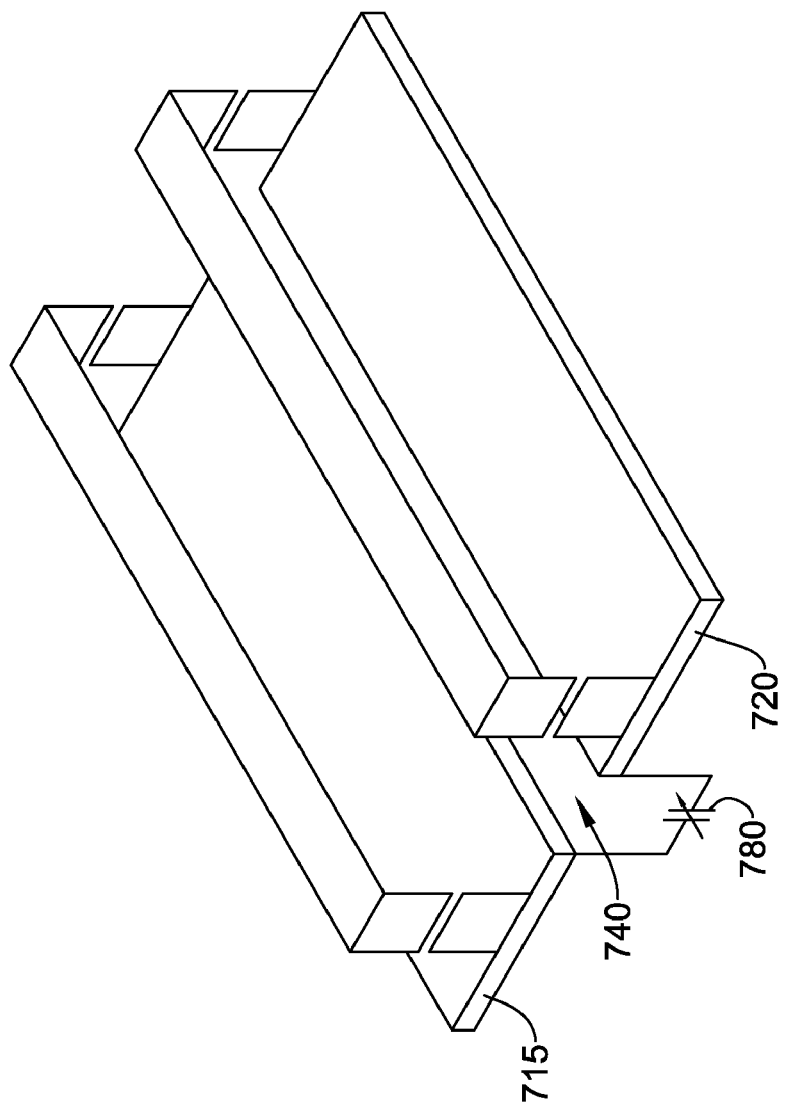
FIG. 7 is a schematic diagram of a computationally simulated RF coil arrangement having discrete capacitive decoupling between distal portions.

Two-Channel Coil Array with Discrete Capacitive Decoupling Between Distal Portions In this example, schematically illustrated in FIG. 7, the geometry is like that of the example of FIG. 5, with the addition of a narrow gap 740 (not to scale) in the shield, physically separating the distal portions 715, 720, and without a bridge capacitor coupling the proximal portions. A discrete decoupling capacitance 780 couples the distal portions 715, 720 and substantially cancels the mutual coupling capacitance between the coil elements. The computed ratio of the induced current to the current in the driven coil element at resonance is $I_2/I_1=4.26\%=-27.4$ dB.

Figure 8:
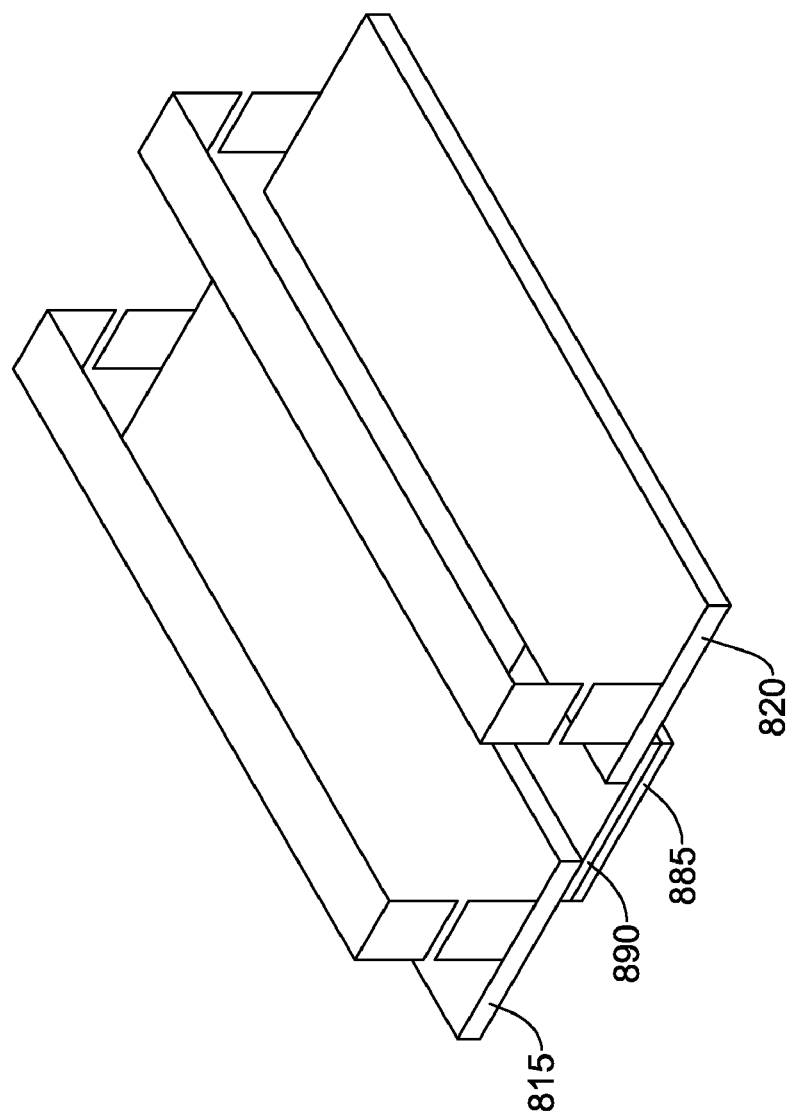
FIG. 8 is a schematic diagram of a computationally simulated RF coil arrangement having distributed capacitive decoupling between distal portions at one end.

Two-Channel Coil Array with Distributed Capacitive Decoupling Between Distal Portions at One End In this example, schematically illustrated in FIG. 8, the geometry is like that of the example of FIG. 7, but without the discrete decoupling capacitance 780. Instead, distributed decoupling capacitance is provided by the introduction of a decoupling patch 885 generally parallel to and overlapping each of distal portions 815 and 820. A decoupling patch is a conducting member and may be formed, for example, from a sheet of metal, which may be copper or any other suitable metal. In the model, a thin layer of dielectric 890 insulates the decoupling patch 885 (conducting member) from the distal portions 815, 820. The decoupling patch 885 in this example is localized at one end of the coil elements, on the same end where drive circuitry (not shown) is coupled to the RF coil. Due to the placement of the decoupling patch adjacent to the distal portions 815, 820 that form, at least in part, the shield of the RF coil, the use of a decoupling patch in this and subsequent examples may be considered shield plate capacitance decoupling, and the decoupling patch(es) may be considered part of the RF coil shield.

In this geometry, and similarly for the geometry of subsequent examples incorporating distributed capacitive decoupling, the overall distributed capacitance between the distal portions 815, 820 includes contributions from distributed capacitances between the first distal portion 815 and the decoupling patch 885 (conducting member), and between the second distal portion 820 and the decoupling patch. This net distributed capacitance may contribute substantially toward the net capacitance between the distal portions 815, 820, and may be selected to substantially cancel the mutual coupling inductance between the coil elements.

In this example, the computed ratio of the induced current to the current in the driven coil element at resonance is $I_2/I_1=1.53\%=-36.3$ dB.

Figure 9:
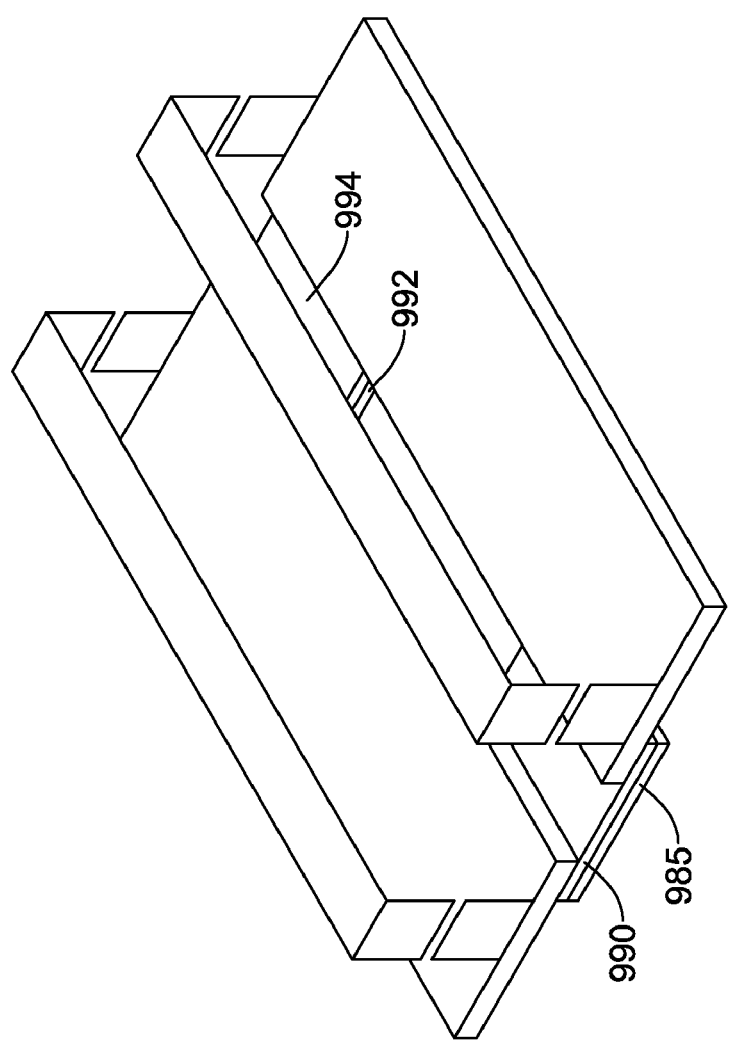
FIG. 9 is a schematic diagram of a computationally simulated RF coil arrangement having distributed capacitive decoupling between distal portions at both ends.

Two-Channel Coil Array with Distributed Capacitive Decoupling Between Distal Portions at Two Ends In this example, schematically illustrated in FIG. 9, the geometry is like that of the example of FIG. 8, with the addition of another decoupling patch 992, separated from the shield distal portions by another portion of dielectric 994. The geometries of the decoupling patches 985, 992 are chosen to substantially cancel the mutual coupling inductance between the coil elements. The computed ratio of the induced current to the current in the driven coil element at resonance is $I_2/I_1=0.99\%=-40$ dB.

Figure 11B:
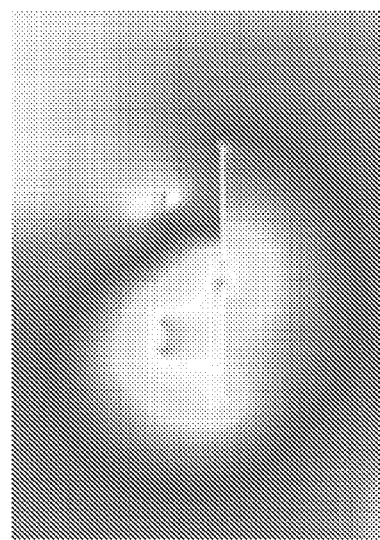
FIGS. 11A and 11B show plan and cross-sectional views, respectively, of the computed $B_1$ field generated by an RF coil configured as in FIG. 9.
Figure 11D:
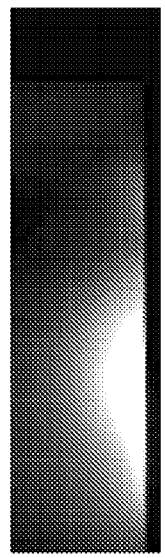
FIGS. 11C and D show corresponding views of actual $B_1$ field measurements in a physical implementation of an RF coil configured as in FIG. 9.
Figure 11A:
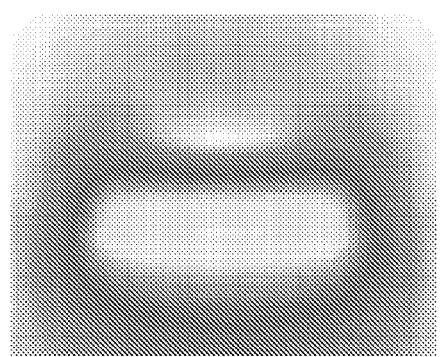
Figure 11C:
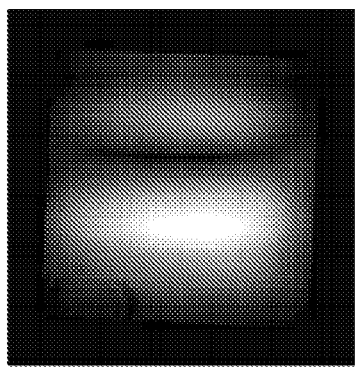

FIGS. 11A and 11B show plan and cross-sectional views, respectively, of the computed $B_1$ field generated by an RF coil configured as in FIG. 9. FIGS. 11C and D show corresponding views of actual $B_1$ field measurements in a physical implementation of this coil design. In FIG. 11B, the proximal and distal portions of the coil elements can be seen. In corresponding FIG. 11D, only the $B_1$ field above the plane of the proximal portions is shown.

Figure 10:
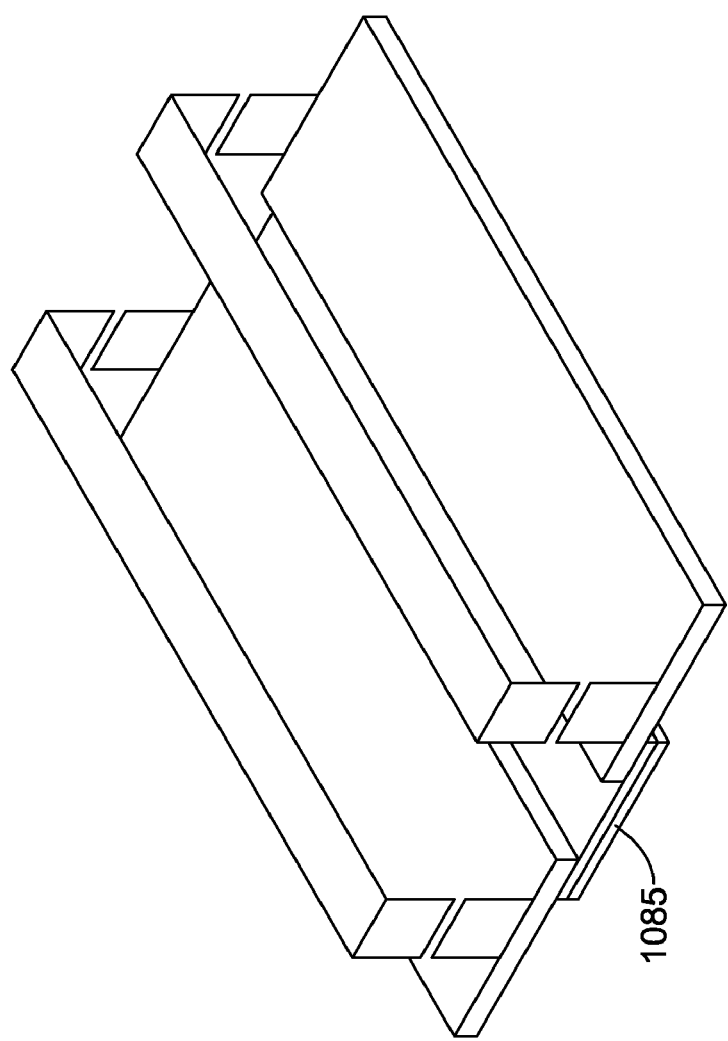
FIG. 10 is a schematic diagram of a computationally simulated RF coil arrangement having distributed capacitive decoupling between distal portions lengthwise.

Two-Channel Coil Array with Distributed Capacitive Decoupling Between Distal Portions Lengthwise In this example, schematically illustrated in FIG. 10, the geometry is like that of the example of FIG. 9, except that the two decoupling patches are replaced by a single decoupling patch 1085 disposed substantially along the entire length of the shield distal portions. The geometry of the decoupling patch 1085 is chosen to substantially cancel the mutual coupling inductance between the coil elements. In addition to decoupling the coil elements, this decoupling patch geometry may advantageously provide additional shielding to the RF coil. The computed ratio of the induced current to the current in the driven coil element at resonance is $I_2/I_1=2.43\%=-32.3$ dB.

In some embodiments, a single decoupling patch with varying width may be disposed along a gap between distal portions. The varying width may have the effect of concentrating capacitance at particular locations along the length of the decoupled coil elements of the RF coil. For example, a "bow-tie" configuration for a decoupling patch, with wider ends and a narrower middle, may be used to provide greater capacitance near the ends of the coil elements. Such a decoupling patch may provide, in effect, a combination of the decoupling arrangements of FIGS. 9 and 10.

16 Channel 7T Body Coil

Figure 12:
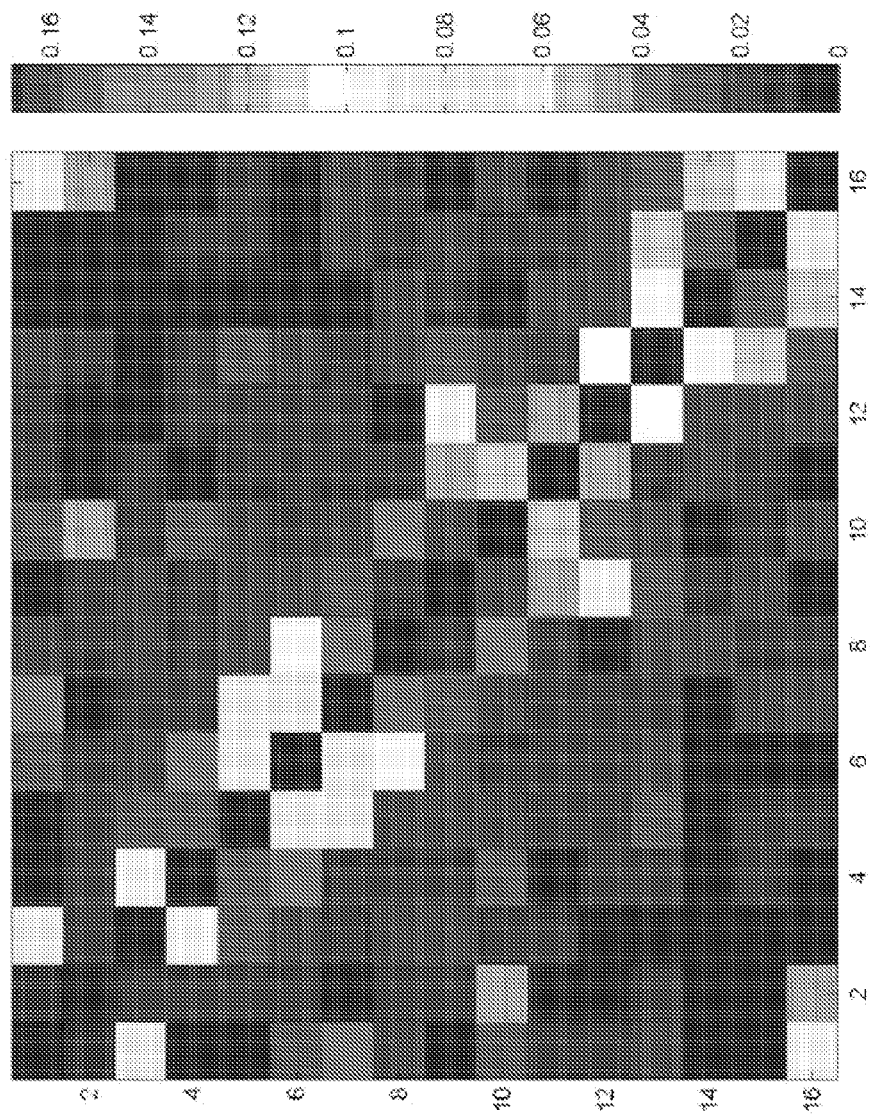
FIG. 12 shows a decoupling matrix for a 16 coil element body coil built with elements decoupled by the methods of this disclosure.
Figure 13:
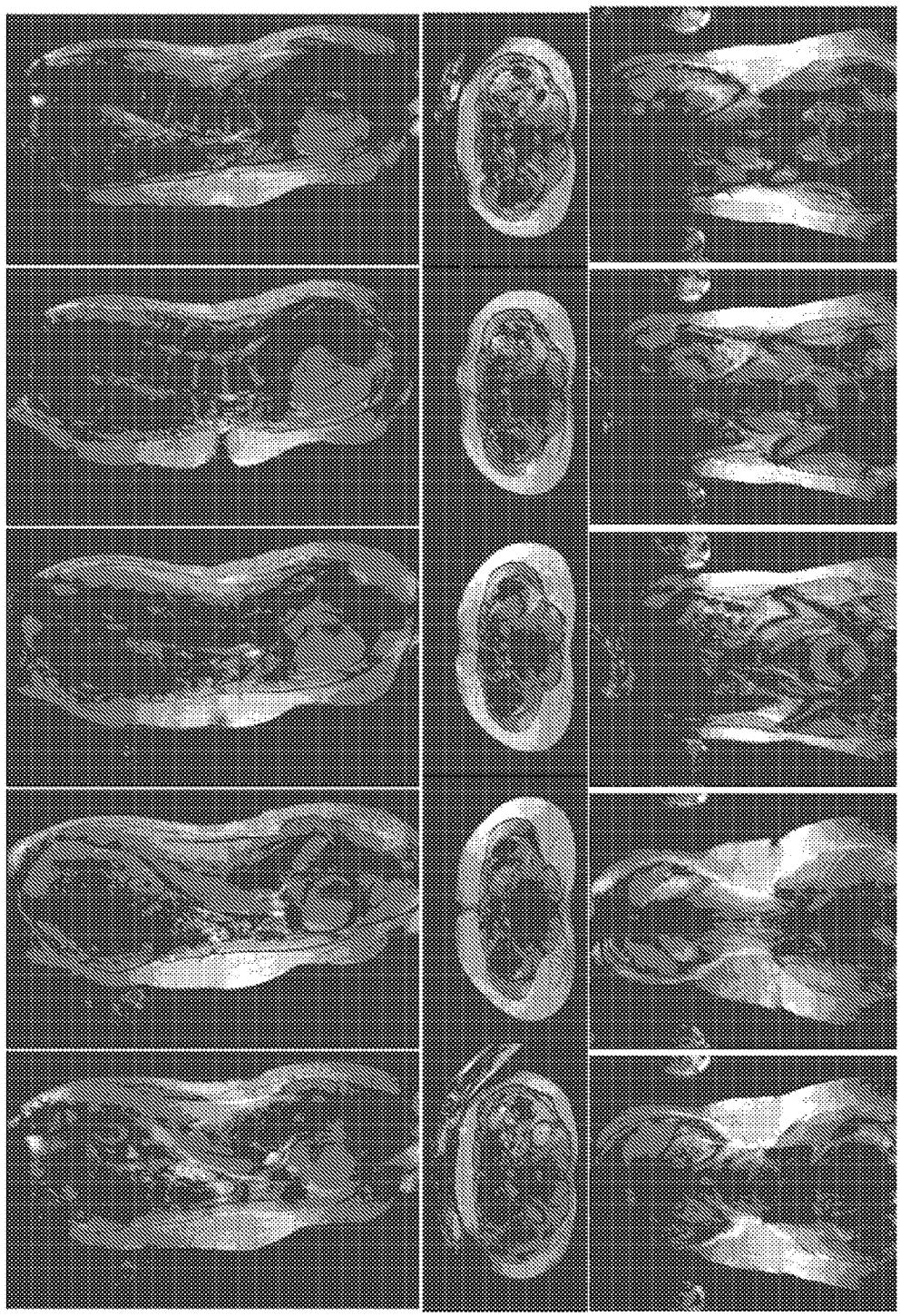
FIG. 13 shows images of a human subject obtained using the coil of FIG. 12.
Figure 14:
FIG. 14 shows comparative images of a human subject using a body coil without coil element decoupling by the methods of this disclosure.

A 16 coil element body coil was built with elements decoupled by the methods of this disclosure. FIG. 12 shows a decoupling matrix for this coil, indicating coupling between any pair of coil elements not greater than about 16%. FIG. 13 shows images of a human subject obtained using this coil. FIG. 14 shows comparative images of a human subject using a body coil without coil element decoupling by the methods of this disclosure.

The disclosure should not be considered limited to the particular examples described above, but rather should be understood to cover all aspects of the invention as set out in the attached claims. Various modifications, equivalent processes, as well as numerous structures to which the invention can be applicable will be readily apparent to those of skill in the art upon review of the instant specification.

What is claimed is:

1. A radio frequency (RF) coil adjacent an imaging region, the RF coil comprising:
   a plurality of conducting coil elements, each conducting coil element including a proximal portion and a distal portion, proximal and distal being relative to the imaging region; and
   a capacitance between the distal portions of the at least two conducting coil elements;
   wherein a mutual coupling inductance between at least two conducting coil elements of the plurality of conducting coil elements is substantially cancelled by the capacitance between the distal portions of the at least two conducting coil elements.

2. The RF coil of claim 1, wherein the distal portion is generally parallel to the proximal portion.

3. The RF coil of claim 1, wherein the capacitance between the distal portions of the at least two conducting coil elements includes a lumped capacitance.

4. The RF coil of claim 1, wherein the capacitance between the distal portions of the at least two conducting coil elements includes a distributed capacitance.

5. The RF coil of claim 4, further comprising:
   a conducting member disposed generally parallel to and overlapping each of the distal portions of the at least two conducting coil elements;
   wherein the distributed capacitance includes secondary distributed capacitances between the conducting member and each of the distal portions of the at least two conducting coil elements; and
   wherein the distributed capacitance contributes substantially to the capacitance between the distal portions of the at least two conducting coil elements.

6. The RF coil of claim 5, further comprising a dielectric material disposed between the conducting member and the distal portions of the at least two conducting coil elements.

7. The RF coil of claim 1, wherein the proximal portions of the at least two conducting coil elements are not directly coupled by a lumped capacitance.

8. The RF coil of claim 1, wherein the at least two of the plurality of conducting coil elements are driven with or receive independent currents.

9. The RF coil of claim 1, wherein each of the plurality of conducting coil elements are driven with or receive a current independent of a remainder of the plurality of conducting coil elements.

10. The RF coil of claim 1, wherein the coil bounds a cavity, the imaging region being within the cavity.

11. The RF coil of claim 10, wherein the coil bounds a substantially cylindrical cavity.

12. The RF coil of claim 1, wherein the imaging region is not bounded by the RF coil.

13. The RF coil of claim 12, wherein the coil is generally flat.

14. The RF coil of claim 1, wherein the mutual coupling inductance between the at least two conducting coil elements has a magnitude of less than 10%.

15. The RF coil of claim 1, wherein the RF coil is a transmit and/or receive coil for a magnetic resonance imaging system.

16. A magnetic resonance imaging system, comprising
a superconducting magnet;
a gradient coil system; and
an RF coil adjacent an imaging region, the RF coil comprising a plurality of conducting coil elements, each conducting coil element including a proximal portion and a distal portion, proximal and distal being relative to the imaging region, and a capacitance between the distal portions of the at least two conducting coil elements; wherein a mutual coupling inductance between at least two of the plurality of conducting coil elements is substantially cancelled by the capacitance between the distal portions of the at least two conducting coil elements.

17. A method for balancing an RF imaging coil having a plurality of independent current elements, the method comprising the steps of:

selecting an RF imaging coil design to achieve specified imaging objectives;
identifying a pair of current elements of the plurality of independent current elements;
modifying distal portions of the pair of current elements to result in a reduced mutual coupling inductance between the pair of current elements below an acceptable threshold inductance value.

18. The method of claim 17, wherein selecting an RF imaging coil design includes selecting a design with a symmetry in the plurality of conducting elements, and further comprising the step of modifying distal portions of additional pairs of current elements of the plurality of independent current elements in a similar manner to the modifying the distal portions of the pair of current elements; wherein the symmetry in the plurality of conducting elements results in reduced mutual inductances between the additional pairs of current elements below the acceptable threshold inductance value.

19. The method of claim 17, wherein modifying the distal portions of the pair of current elements includes modifying a capacitance between the distal portions.

20. The method of claim 17, wherein modifying a capacitance between the distal portions includes increasing a distributed capacitance between the distal portions.

* * * * *

UNITED STATES PATENT AND TRADEMARK OFFICE
CERTIFICATE OF CORRECTION

| | | |
|---|---|---|
| PATENT NO. | : 8,380,266 B2 | Page 1 of 1 |
| APPLICATION NO. | : 13/124206 | |
| DATED | : February 19, 2013 | |
| INVENTOR(S) | : J. Thomas Vaughan and Jinfeng Tian | |

It is certified that error appears in the above-identified patent and that said Letters Patent is hereby corrected as shown below:

In the Specifications:

In Column 1, Lines 11 to 16, delete the following:

"GOVERNMENT RIGHTS

The present subject matter was partially supported under NIH contract numbers EB000895-04 and EB006835. The United States government may have has certain rights in the invention."

and add the following:

--GOVERNMENT INTEREST

This invention was made with government support under EB000895-04 and EB006835 awarded by the National Institutes of Health. The government has certain rights in the invention.--

Signed and Sealed this
Twenty-third Day of April, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,380,266 B2  
APPLICATION NO. : 13/124206  
DATED : February 19, 2013  
INVENTOR(S) : J. Thomas Vaughan et al.

It is certified that error appears in the above-identified patent and that said Letters Patent is hereby corrected as shown below:

In the Specifications:

Col. 1, line 15, delete "may have"

Col. 1, line 28, delete "(MM)" and add -- (MRI) --

Col. 1, line 59, delete "process" and add -- precess --

Col. 1, line 61, delete "processing" and add -- precessing --

Col. 2, line 1, delete "processing" and add -- precessing --

Signed and Sealed this  
Twenty-first Day of May, 2013

Teresa Stanek Rea  
*Acting Director of the United States Patent and Trademark Office*